US007182773B2

(12) United States Patent
Bouchier

(10) Patent No.: US 7,182,773 B2
(45) Date of Patent: Feb. 27, 2007

(54) CAVITY MEASUREMENT DEVICE AND METHOD OF ASSEMBLY

(75) Inventor: Mark Bouchier, Lakeville, MN (US)

(73) Assignee: AMS Research Corporation, Minnetonka, MN (US)

( * ) Notice: Subject to any disclaimer, the term of this patent is extended or adjusted under 35 U.S.C. 154(b) by 722 days.

(21) Appl. No.: 10/310,496

(22) Filed: Dec. 5, 2002

(65) Prior Publication Data

US 2003/0083690 A1 May 1, 2003

Related U.S. Application Data

(62) Division of application No. 09/300,238, filed on Apr. 27, 1999, now Pat. No. 6,533,799.

(51) Int. Cl.
*A61M 29/00* (2006.01)
(52) U.S. Cl. .................................... 606/192
(58) Field of Classification Search ............ 604/96.01, 604/104, 97.01, 103.05, 103.03, 103.06, 604/915, 921; 156/86, 81, 264, 291; 264/230; 29/447; 606/194, 192
See application file for complete search history.

(56) References Cited

U.S. PATENT DOCUMENTS

| 3,861,972 A | | 1/1975 | Glover et al. | |
| 4,147,169 A | | 4/1979 | Taylor | |
| 4,213,461 A | | 7/1980 | Pevsner | |
| 4,227,293 A | * | 10/1980 | Taylor | 29/447 |
| 4,335,723 A | | 6/1982 | Patel | |
| 5,195,969 A | * | 3/1993 | Wang et al. | 604/96.01 |
| 5,254,089 A | | 10/1993 | Wang | |
| 5,344,402 A | | 9/1994 | Crocker | |

(Continued)

FOREIGN PATENT DOCUMENTS

WO   WO 92/20280 A   11/1992

(Continued)

OTHER PUBLICATIONS

Howmedica, *Cavity Measurement Device*, Phase II Report, Design Review No. 2, Feb. 3, 1998, VIR Engineering, Medical Products Development, Santa Barbara, CA.

(Continued)

*Primary Examiner*—Nicholas D. Lucchesi
*Assistant Examiner*—Christopher D Koharski
(74) *Attorney, Agent, or Firm*—Jose' W. Jimenez; Kimberly K. Baxter

(57) ABSTRACT

A design and method of manufacture are disclosed for a cavity measurement device used during surgical procedures. The cavity measurement device includes an inflation tube assembly comprising an elongated tube having a distal end and a proximal end and a balloon mounted at the distal end of the elongated tube. The elongated tube and the balloon comprise dissimilar materials and include an adhesive free seal between the elongated tube and the balloon. The inflatable balloon is inserted into a cavity and inflated with a volume of fluid, whereby the balloon volume represents the cavity volume. The mechanical attachment of the balloon onto the tube is substantially leakproof and has an attachment strength greater than the balloon material tensile strength. The mechanical attachment of the present invention substantially eliminates the potential for bond separation and preparatory operations typically associated with adhesive bonds.

20 Claims, 3 Drawing Sheets

U.S. PATENT DOCUMENTS

| | | | |
|---|---|---|---|
| 5,366,442 A | 11/1994 | Wang et al. | |
| 5,425,710 A | 6/1995 | Khair et al. | |
| 5,868,707 A | 2/1999 | Williams | |
| 6,227,077 B1 * | 5/2001 | Chiang | 81/63.1 |
| 6,533,799 B1 | 3/2003 | Bouchier | |

FOREIGN PATENT DOCUMENTS

| | | |
|---|---|---|
| WO | WO 95/26689 A1 | 10/1995 |
| WO | WO 97/42871 A | 11/1997 |

OTHER PUBLICATIONS

Spinal Degeneration, Arnot Ogden Medical Center, Article (2 pages) 1996 http://www.aomc.org/HOD2/general/back-Spinaldegen.html.

Herniated Disc, The Joint Section of Spine and Peripheral Nerves of The American Association of Neurological Surgeons and Congress of neurological Surgeons, Article (3 pages) 1990 http://www.neurosurgery.org/pubpages/patres/herniatedbroch.html.

Lumbar Miscrodiskectomy, Ludann Education Services, Article, 2 pages, date unknown http://www.ludann.com/1_1621_Bac1213_LumbarMicro.html.

Lumbar Disc Disease, NYU Department of Neurosurgery, (2 pages) Jan. 27, 1996, http://www.mens10.med.nyu.edu/spine/spine_surgery_p2.html.

The Collaborative Practice of Neurosurgery, Microendoscopic Disectomy, Article (3 pages) date unknown http://www.drgrin.com/drgrin/B_Neurosurgery/B1_EndoDisc.html.

* cited by examiner

CAVITY MEASUREMENT DEVICE AND METHOD OF ASSEMBLY

This application is a divisional of U.S. Pat. application Ser. No. 09/300,238, filed Apr. 27, 1999 now U.S. Pat. No. 6,533,799.

FIELD OF THE INVENTION

The present invention relates generally to a cavity measurement device used during surgical procedures and a method of assembling a cavity measurement device. The present invention particularly relates to inflation tubes with a balloon used during surgery and methods of attaching a balloon to an inflation tube.

BACKGROUND OF THE INVENTION

The main structural support of the human skeleton is the spine which is the bone structure that extends from the base of the skull to the pelvis. It includes a spinal cord which is approximately eighteen inches in length and comprised of nerves that carry impulses to and from the brain to the rest of the body.

Surrounding the spinal cord are pairs of rings of bone called vertebrae which constitute the spinal column (back bones) and each pair of vertebrae is connected by a flexible joint that stabilizes the vertebrae and allows the spine to move.

An "intervertebral disk"—or simply the "disk"—is located between each pair of vertebrae within the flexible joint and bears most of the compressive load of the spinal column. Each disk is a flat, circular capsule approximately one inch in diameter and has an outer layer or membrane which is strong and flexible and comprised of a fibrous cartilage called the annulus fibrosis. It also has an inner core which consists of a soft, gelatinous substance called the nucleus pulposus. The main function of the disk is to cushion the vertebrae during movement.

The structure of the human spine is designed for an upright position, a typical posture for humans throughout history, where walking, running, hunting, gathering, working on farms or at workbenches were common body motions and positions. Today, a high proportion of people lead sedentary lives, spending the better part of each day sitting behind desks writing patent applications, at work stations, in automobiles, etc. These changes in human behavior overtime, mainly resulting from technological advances, have had a profound and largely negative impact on human physiology, and particularly the spine. As a result, spine or back problems are the most common physical complaints among adults.

Everyday physical stresses and the normal aging process also adversely affect the human spine. In that connection, one of the most common back problems experienced by adults results from degenerative disk disease, a general term applied to degeneration of the intervertebral disks. As the body ages, the disk material loses its elasticity and hardens, developing a consistency similar to a piece of hard rubber.

A specific example of degenerative disk disease is a herniated disk which is a condition resulting from strain or injury to the disk that causes the inner material of the disk to swell or herniate and the outer layer to rupture. When the disk ruptures, the inner material bulges and presses against, or pinches, the spinal nerves, resulting in severe pain.

When the disk degenerates to the point where it no longer properly functions, the disk is removed during a procedure called a diskectomy. A diskectomy involves removal of the ruptured or diseased disk from its location between adjacent vertebrae. By removing the disk and any associated disk or bone fragments, the source of the pressure on the spinal nerve is also removed, thereby relieving the pain.

Following a diskectomy, the adjacent vertebrae may be fused together, resulting in partial loss of spinal flexibility. On the other hand, a bone graft or other specialized material, such as a prosthetic intervertebral implant, may be placed in the empty disk space in order to stabilize the vertebrae.

Bone grafts and similar prosthetic implants used following diskectomy require the implant and surrounding vertebrae to be shaped using precision drilling and shaving techniques in order to provide a proper fit with the implant. This type of surgical reconstruction is difficult and time-consuming and often still results in limited flexibilty of the spine. As a result, synthetic intervertebral disk prostheses have been developed such as those described in U.S. Pat. No. 4,863,477. These synthetic prostheses are fabricated prior to performance of the surgery and are shaped during surgery to conform specifically to the shape of the disk space, thereby eliminating the tedious task of precision drilling and shaving techniques associated with bone implants. Moreover, these synthetic prostheses provide a resiliency that facilitates flexibility of the spine.

In order to ensure that the prosthetic incorporates the proper shape and volume for the target space, various measuring techniques have been proposed. These techniques include X-rays, magnetic resonance imaging (MRI), computed tomography (CT) scans and myelography, a radiological technique for viewing the spinal cord. These techniques, although quite useful, are not without certain drawbacks including high costs, potential adverse side effects and inherent measuring inaccuracies which result from a variety of factors, including high signal to noise ratios, limited two-dimensional images, and potential radiation exposure. Furthermore, these devices are expensive and require highly-skilled technicians to operate them properly.

As a result, practitioners and medical institutions have continually sought a lower cost and less complex method of obtaining the data necessary to fabricate a quality prosthetic. In particular, there is a desire to obtain low-cost vet highly accurate body cavity measuring device that can be used with minimal to no side effects. Such a device must be biocompatible, non-toxic and simple to use. Finally, such a device must be fabricated by a manufacturing method that is efficient, easy to implement and cost effective.

OBJECTS AND SUMMARY OF THE INVENTION

In view of the foregoing, it is an object of the present invention to provide a cavity measurement device that addresses the drawbacks associated with prior art cavity measuring devices, yet meets the needs of the users.

A further object of the present invention is to provide a cavity measurement device that is biocompatible, non-toxic and simple to use.

A further object of the present invention is to provide a cavity measurement device that provides a leakproof attachment of an inflatable balloon to a tube or cannula.

A further object of the present invention is to provide a cavity measurement device that provides a leakproof attachment able to withstand a 45 psi balloon pressure during use.

A further object of the present invention is to provide a cavity measurement device that includes a mechanical attachment with an attachment strength greater than the balloon material tensile strength.

A further object of the present invention is to provide a method of making a cavity measurement device that is efficient, easy to implement and cost effective.

These and other objects not specifically enumerated herein are believed to be addressed by the present invention which contemplates a cavity measurement device that includes an inflation tube assembly comprising an elongated tube having a distal end and a proximal end and a balloon mounted at the distal end of the elongated tube. The elongated tube and the balloon comprise dissimilar materials and include an adhesive free seal between the elongated tube and the balloon.

The present invention also contemplates a method of assembling a cavity measurement device which may include the steps of attaching a silicone inflatable balloon having a tubular stem section and a bulbous section onto an elongated thermoplastic tube by sliding the stem section onto an end of the elongated tube and positioning a piece of heat-shrink tube over an area of the stem section that overlaps the elongated tube. The next steps may include shrinking the heat shrink tube and folding a length of the stem section over the heat-shrink tube. The following steps would include overlaying a compression tube onto an overtube so as to create an overtube assembly and aligning the overtube assembly onto the stem section and a portion of the elongated tube. The next steps would likely include heating and subsequently cooling the overtube assembly so that the compression tube molds the overtube onto the stem section and elongated tube. The final steps would include bonding an end of the overtube onto the elongated tube, thereby forming a mechanical, leakproof bond, and removing the compression tube.

BRIEF DESCRIPTION OF THE DRAWINGS

Other features and advantages of the present invention will be seen as the following description of particular embodiments progresses in conjunction with the drawings, in which.

DETAILED DESCRIPTION OF THE INVENTION

Figure 1:
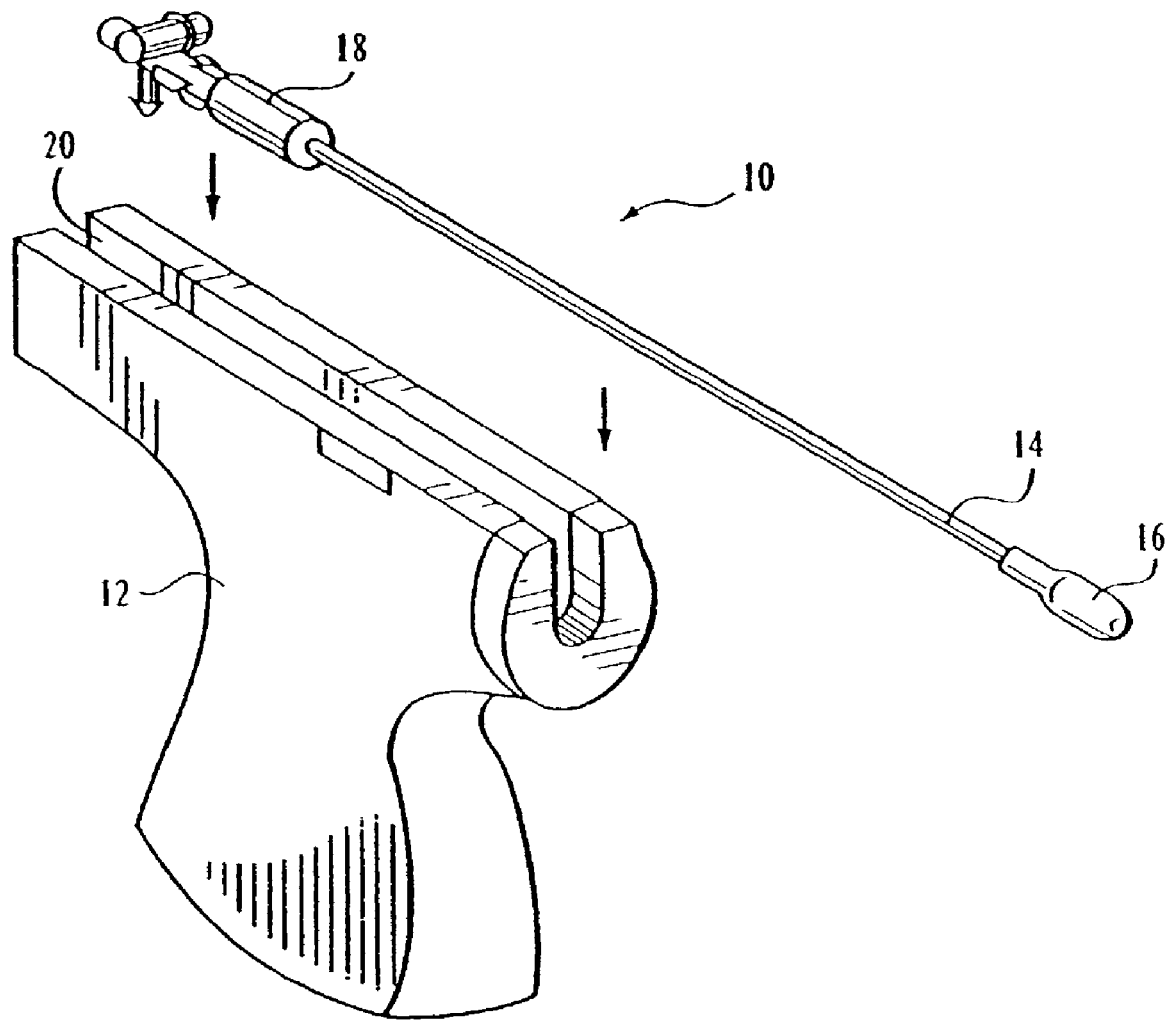
FIG. 1 is a perspective view of a cavity measurement device in accordance with a preferred embodiment of the present invention.

Referring to FIG. 1, an embodiment of a cavity measurement device 10 for use with a pistol-grip handle 12 or other similar device in accordance with the present invention includes an elongated inflation tube or cannula 14 and an inflatable balloon 16. The inflatable balloon 16 is mechanically affixed to one end of the elongated tube 14 and provides a leakproof attachment that can withstand a 45 psi balloon pressure. The other end of the elongated tube 14 connects to a balloon mount 18 that couples onto the trigger receptacle 20 of the handle 12.

Figure 2:
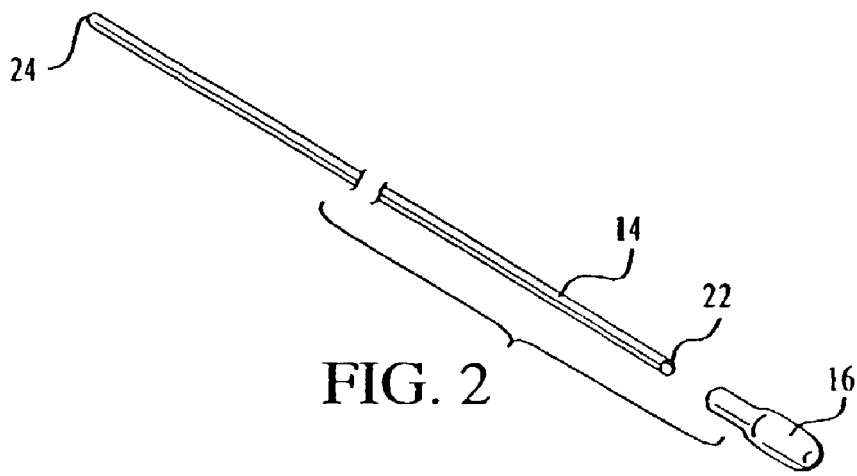
FIG. 2 is a second perspective view of a cavity measurement device in accordance with a preferred embodiment of the present invention.

Referring to FIG. 2, an embodiment of the elongated tube 14 includes a distal end 22 and a proximal end 24. The distal end 22 of the elongated tube 14 connects to the inflatable balloon 16 and the proximal end 24 of the elongated tube 14 connects to the balloon mount 18 (not shown). The inner diameter of the elongated tube 14 should be large enough to adequately support a flow of fluid and is commonly between the range of 3–4 French. Since a portion of the elongated tube 14 is inserted into a body space, the outer diameter of the elongated tube 14 should be large enough to accommodate the flow of fluid in its inner diameter, yet small enough so as to be minimally invasive during a surgical procedure. A suitable outer diameter for the elongated tube 14 is about 7 French to 8 French.

The elongated tube 14 should be long enough so that a first section of the elongated tube 14 adequately fits into the trigger receptacle 20 (not shown) and the remaining section of the elongated tube 14 extends sufficiently beyond the trigger receptacle 20. For the cavity measurement device 10 of the present invention, the length of the elongated tube 14 is typically about 38 cm to 40 cm. The section of elongated tube 14 extending beyond the trigger receptacle 20 must be of optimal length, such as 20 cm, to allow a portion of the elongated tube 14 to be inserted into the body between the vertebrae of a spine during a diskectomy or similar procedure.

Since a portion of the elongated tube 14 will contact the body, its material should be biocompatible and non-toxic. In a preferred embodiment, the material of the elongated tube 14 is a thermoplastic, such as polyethylene terephthalate (PET). Similar materials, such as nylon, may also be used.

The fabrication of the elongated tube 14 typically involves an extrusion process that provides precisely controlled inner diameters and wall-thicknesses. The particular configuration of the elongated tube 14 provides sufficient rigidity to withstand the forces and pressures exerted on it during a surgical procedure.

Figure 3:
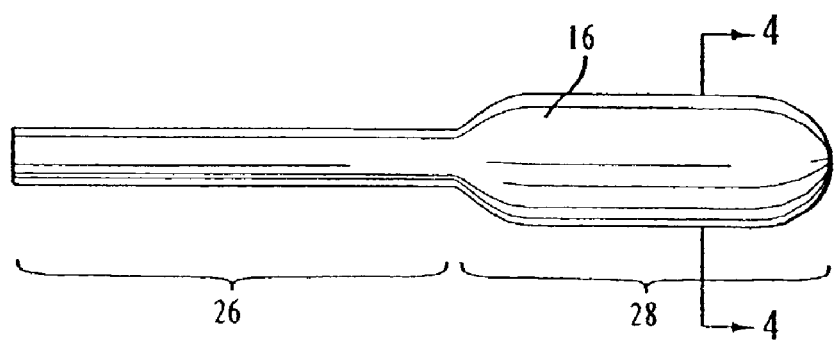
FIG. 3 is a side perspective view of an inflatable balloon component of the cavity measurement device in accordance with a preferred embodiment of the present invention.

As shown in FIG. 3, the cavity measurement device 10 of the present invention also includes an inflatable balloon 16. In a preferred embodiment, the inflatable balloon 16 is made of an elastic material, such as silicone, that is capable of being easily stretched or expanded and resuming its former shape. The preferred balloon 16 material is silicone because of its low durometer and high tear resistance (i.e. elongation at break) biocompatibility and non-toxicity. Silicone is also preferred due to its high elasticity and low modulus of elasticity which enables the balloon to conform substantially to the inner surfaces of the cavity being measured. An example of such a silicone is MED 10-6640 made by NuSil.

Other types of typical balloon materials, such as polyurethane, do not have sufficient elasticity to enable the proper degree of conformance to the inner surfaces.

The inflatable balloon 16 includes a tubular stem section 26 and a bulbous portion 28. The stem section 26 and bulbous portion 28 are located at the proximal and distal ends, respectively, of the inflatable balloon 16. In a preferred embodiment, the length of the stem section 26 is about 1.9 cm. Additionally, the length of the bulbous portion 28 of the inflatable balloon 16 is typically 1.2 cm.

In its unassembled state, as show in FIG. 3, the inner diameter of the stem section 26 of the inflatable balloon 16 is approximately 0.25 mm. The diameter of the stem section 26, together with its material elasticity, enable the stem section 26 to be easily mounted onto the distal end 22 of the elongated tube 14. This particular configuration ensues uniform surface contact between the inner surface of the stem section 26 and the outer surface of the elongated tube 14. In addition, the thickness of the inflatable balloon 16 material is relatively uniform alone its entire length so as to allow uniform inflation when a fluid is introduced. However, in an alternate embodiment the material thickness of the inflatable balloon 16 may be variable along its length depending on the various desired inflation characteristics and surgical procedure to be performed.

To minimize potential damage to surrounding tissues when the cavity measurement device 10 is inserted into the body cavity during a surgical procedure, the ouer surface of the inflatable balloon 16 is relatively smooth. In a preferred embodiment, the bulbous portion 28 of the inflatable balloon 16 is relatively oblong in shape, allowing for easy insertion into a body cavity such as a disk space. Alternative geometries for the bulbous portion 28 include, but are not limited to, oval, spherical, tubular and barrel-shaped. The particular geometry chosen is typically based upon the body cavity shape and type of surgical procedure performed.

Figure 4:
FIG. 4 is a cross-sectional view of an inflatable balloon taken along the lines 4—4 in FIG. 3.

As shown in FIGS. 3 and 4, when configured in an oval geometry, the bulbous portion 28 has a center diameter of approximately 9.5 French. However, the center diameter of the bulbous portion 28 can range from 8 to 10.5 French, or any suitable size that allows the cavity measurement device 10 to be inserted into a body cavity. Typically, the center diameter of the bulbous portion 28 is greater than the inner and/or outer diameters of the stem section 26 of the inflatable balloon 16.

Turning next to how the balloon 16 is mounted to the elongated tube 14, it is important to note that conventional adhesives are ineffective bonding agents in this context due to the dissimilar material characteristics of the inflatable balloon 16 and elongated tube 14. Such adhesives are typically unable to withstand the high pressures exerted on the bond by the inflatable balloon 16. In addition, the elasticity of the inflatable balloon 16 tends to be compromised by the rigid bond caused by chemical adhesives. As a result, such bonds have a tendency to separate or peel away when subject to various stresses and pressures encountered during surgical procedures.

As a result, in the present invention, a mechanical fixation method is used. The mechanical fixation provides a durable leakproof attachment of the inflatable balloon 16 to the elongated tube 14 which, in a preferred embodiment is capable of withstanding a 45 psi balloon pressure and is greater than the balloon 16 material tensile strength. In addition, the use of a mechanical fixation method avoids pre-surface treatments, primers cure times, or other preparatory operations typically associated with adhesive bonding methods.

Figure 5:
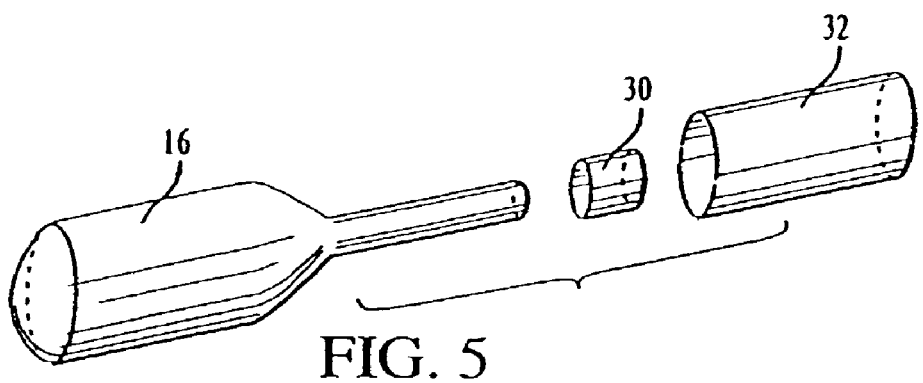
FIG. 5 is a perspective view of an inflatable balloon attachment assembly in accordance with a preferred embodiment of the present invention.

Referring to FIG. 5, the structure used to mechanically attach the balloon 16 to the tube 14 is shown and includes a heat-shrink tube 30 and an overtube 32. The heat-shrink tube 30 is used to mechanically attach the inflatable balloon 16 to the elongated tube 14. More specifically, the heat-shrink tube 30 is positioned onto a portion of the stem section 26 of the balloon 16 that is mounted onto the elongated tube 14. Heat is then applied to the heat-shrink tube 30 which causes it to shrink and conform to the size and shape of that portion of the stem section 26 and the elongated tube 14, thereby securing the stem section 26 to the elongated tube 14.

In a preferred embodiment, the heat-shrink tube 30 is made of polyvinylidene fluoride (PVDF). Alternatively, the heat-shrink tube 30 may be fabricated from other suitable heat-shrink materials, such as polyolefin and teflon The heat-shrink tube 30 is approximately 0.4 cm long, with an internal diameter of about 0.3 cm. The internal diameter of the heat-shrink tube 30 must be of sufficient size to allow the heat-shrink tube to fit, prior to heating, over the stem section 26 of the inflatable balloon 16 when it is mounted onto the elongated tube 14.

In addition to use of the heat shrink, an overtube 32 of the present invention is also used to assist in mechanically fixating the inflatable balloon 16 onto the elongated tube 14. A description of how the overtube 32 is utilized is set forth below. The overtube 32 also softens when subject to heat and is preferably made from polyethylene terephthalate (PET). Alternatively, the overtube 32 may be fabricated from nylon or other similar materials that are conformable when heat is applied.

In addition to the particular material attributes of the overtube 32, the dimensional configuration of the overtube 32 is also important in order to obtain the necessary mechanical bonding of the balloon 16 to the elongated tube 14. The inner diameter and length of the overtube 32 should be appropriately sized to allow the overtube 32 to surround and overlap the assembled heat-shrink tube 30, stem section 26 and a portion of the elongated tube 14. In a preferred embodiment, the length and inner diameter of the overtube 32 are 1.9 cm and 0.38 cm respectively.

Prior to use, the cavity measurement device 10 is primed by evacuating the air from the inflatable balloon 16 and elongated tube 14 and infusing a fluid therein. The fluids used during the priming procedure include, but are not limited to, water, saline and contrast media. It is important to note that these same fluids can also be used as inflation fluids when the device is inserted into a body cavity during a measurement procedure. The objective of the priming procedure is to remove any and all air from the inflatable balloon 16 and elongated tube 14 to ensure accurate volume measurements by the cavity measurement device 10. After the priming procedure is completed, the fluid is removed.

In use during a surgical procedure such as measuring a disk space volume, the inflatable balloon 16, in a deflated state, is inserted into the disk space. Fluid is infused into the balloon 16 causing the balloon 16 to inflate and fill the disk space volume. The volume of fluid infused into the cavity measurement device 10 must attain a predetermined pressure within the disk space that is substantially equivalent to the normal anatomical pressures exerted on a natural intervertebral disk. The amount of fluid volume infused into the cavity measurement device is calculated and a prosthetic disk of equivalent volume is then selected for insertion into the disk space. A preferred prosthetic disk is a hydrogel disk, although other similar prosthetic disks may be used. When inserted into the disk space, the prosthetic disk conforms to the configuration of the cavity and fills the cavity with a sufficient volume of material to create appropriate pressures in the spine to support the body.

Method of Fabrication

The present invention also contemplates a method of fabricating a cavity measuring device and particularly contemplates a method of mechanical fixation of the inflatable balloon 16 onto the elongated tube 14 of the cavity measurement device 10, as shown in FIGS. 6–10. To keep the lumen of the elongated tube 14 open during the assembly procedure, a straight, rigid mandrel 33, preferably made from Nitinol wire, is inserted into the lumen. The mandrel 33 is approximately 1.04 mm in diameter and extends along the length, and slightly beyond the ends 22,24, of the elongated tube 14. The first step of assembling the device of the present invention includes sliding the stem section 26 of the inflatable balloon 16 onto the distal end 22 of the elongated tube 14 such that the entire length of the stem section 26 is placed onto the elongated tube 14. In a preferred embodiment the bulbous portion 28 of the inflatable balloon 16 does not contact and extends beyond the distal end 22 of the elongated tube 14. Therefore, the bulbous portion 28 of the inflatable balloon 16 abuts the distal end 22 of the elongated tube, thereby forming a junction between the stem section 26 and the bulbous portion 28.

Figure 6:
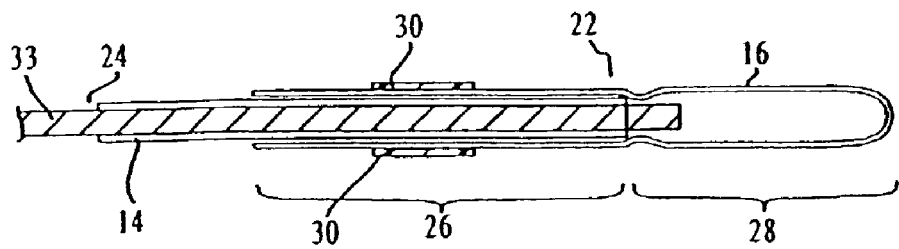
FIG. 6 is a cross-sectional side view of a step of a method of assembling a cavity measurement device in accordance with a preferred embodiment of the present invention.

The next step includes mounting a heat-shrink tube 30 onto an area of the stem section 26, as shown in FIG. 6. Preferably, the inner diameter of the heat-shrink tube 30 is smaller than the outer diameter of the bulbous portion 28 and larger than the outer diameter of the stem section 26 of the inflatable balloon 16. The heat-shrink tube 30 is mounted onto the elongated tube 14 at the proximal end 24 of the elongated tube 14, advanced along the length of the elongated tube 14 and positioned on the stem section 26 of the inflatable balloon 16. In particular, the heat-shrink tube 30 is located on an area of the stem section 26 that allows a sufficient length of stem section 26 to extend beyond the heat-shrink tube 30 toward the proximal end 24 of the elongated tube 14. The length of stem section 26 extending beyond the heat-shrink rube 30 should preferably be greater than the overall length of the heat-shrink tube 30.

The heat-shrink tube 30 is secured onto the stem section 26 using heat which causes the tube 30 material to contract and conform to the shape of the object it surrounds namely, the balloon 16 and the tube 14. After the heat is removed, the heat-shrink tube 30 retains its newly conformed shape, as shown in FIG. 6, and forms a uniform thickness and contact surface with the stem section 26. In addition, the diminished inner diameter size of the heat-shrink tube 30 presses upon the outer diameter of the stem section 26, forming a mechanical fixation.

Figure 7:
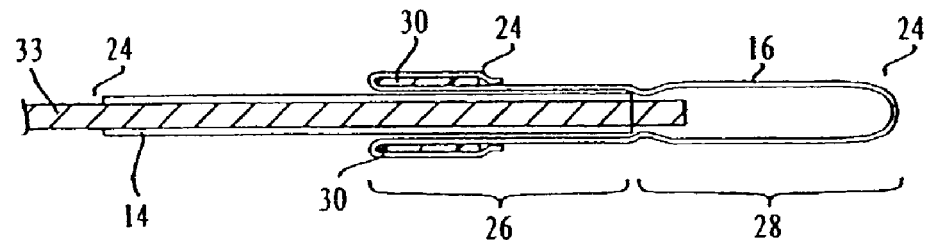
FIG. 7 is a cross-sectional side view of a step of a method of assembling a cavity measurement device in accordance with a preferred embodiment of the present invention.

After shrinking the tube 30 onto the elongated tube 14, the length of the stem section 26 of the balloon 16 that extends past the heat shrink tube 30 toward the proximal end 24 of the elongated tube 14 is folded over the heat-shrink tube 30. In a preferred embodiment, the folded portion of the stem section 26 completely overlaps and partially extends beyond the distal end of the heat-shrink tube 30, as shown in FIG. 7, so that a secure fixation is formed.

Figure 8:
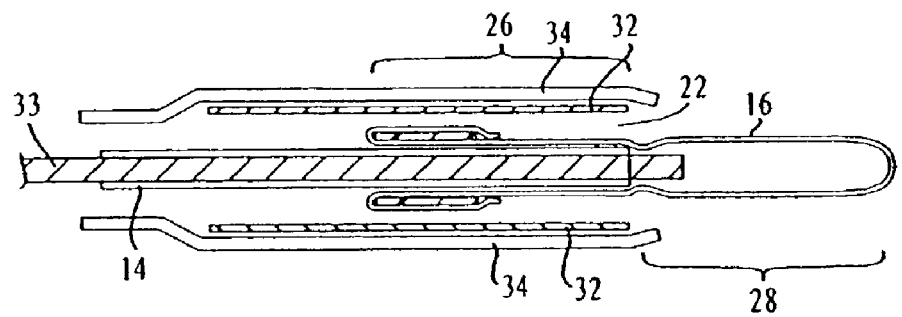
FIG. 8 is a cross-sectional side view of a step of a method of assembling a cavity measurement device in accordance with a preferred embodiment of the present invention.

As shown in FIG. 8, an overtube 32 and a compression tube 34 are then introduced in the form of an overtube assembly. The compression tube 34 is preferably made of silicone, however other similar materials may be used.

In particular, the overtube assembly includes a compression tube 34 with an overtube 32 located internally of the compression tube 34. The overtube assembly is made by radially expanding the compression tube 34 using a flow of fluid, such as air, to increase the inner diameter of the compression tube 34. The overtube 32 is then inserted in the lumen of the compression tube 34 and the flow of fluid is discontinued so that the inner surface of the compression tube 34 uniformly contacts the outer surface of the overtube 32 but remains expanded (due to the overtube 32) beyond its otherwise unstressed configuration.

The overtube assembly is next positioned over the stem section 26 of the balloon and a portion of the elongated tube 14 such that the distal end of the overtube assembly is aligned with the junction formed by the elongated tube 14 and the bulbous portion 28 of the inflatable balloon 16. A portion of the overtube assembly extends beyond the stem section 26 toward the proximal end of the elongated tube 14.

Figure 9:
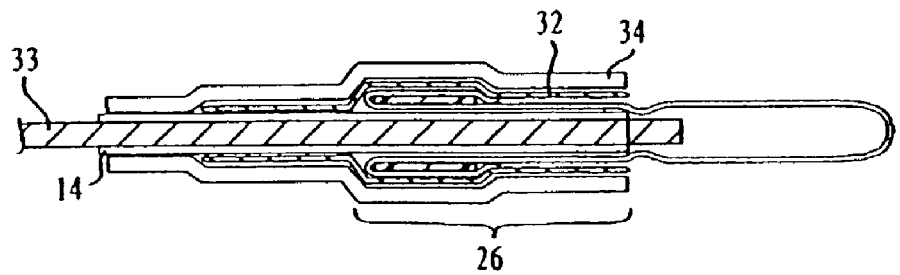
FIG. 9 is a cross-sectional side view of a step of a method of assembling a cavity measurement device in accordance with a preferred embodiment of the present invention.

After the overtube assembly is properly aligned onto the stem section 26 and elongated tube 14, heat is applied to the assembly which causes the overtube 32 to soften. In its softened state, the overtube 32 offers less radial resistance to the compression force exerted by the compression tube 34 thereby allowing the compression tube 34 to compress and conform the overtube 32 to the configuration of the stem section 26 and elongated tube 14, as shown in FIG. 9. After the heat is removed and the assembly allowed to cool, the overtube 32 remains in its conformed configuration, thereby forming a mechanical fixation that further secures the fixation formed by the balloon and the heat shrink tube 30. In a preferred embodiment, the inner surface of the overtube 32 uniformly contacts the outer surface of a portion of the elongated tube 14 and the entire length of the stem section 24 of the inflatable balloon 16. Although the compression tube 34 has now been allowed to return to its substantially unexpanded state, it remains on the assembly and is used to mask and protect the overtube 32 from the hot dyes used during the melt bonding process discussed below.

Figure 10:
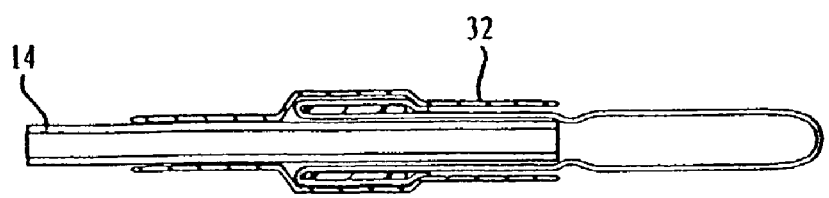
FIG. 10 is a cross-sectional side view of a step of a method of assembling a cavity measurement device in accordance with a preferred embodiment of the present invention.

The final assembly step includes securing a proximal end of the overtube 32 onto the elongated tube 14 by melt bonding the proximal end of the overtube 32 onto the elongated tube 14 thereby forming a clamp bond as shown in FIG. 10. The clamp bond secures the overtube 32 to the elongate tube 14 and prevents the overtube 32 from slipping off of the elongate tube 14 during use of the device. In addition the clamp bond also creates a mechanical, leakproof barrier between the overtube 32 and the elongated tube 14. After the overtube 32 is firmly secured onto the elongated tube 14 and stem section 26 of the inflatable balloon 16, the compression tube 34 and mandrel 33 are removed.

Although the invention has been described in terms of particular embodiments and applications, one of ordinary skill in the art, in light of this teaching, can generate additional embodiments and modifications without departing from the spirit of or exceeding the scope of the claimed invention accordingly, it is to be understood that the drawings and descriptions herein are proffered by way of example to facilitate comprehension of the invention and should not be construed to limit the scope thereof.

What is claimed is:

1. A method of assembling a cavity measurement device comprising the steps of:

attaching a silicone balloon having a tubular stem section and a bulbous portion onto an elongated tube by sliding said stem section onto a distal end of said elongated tube;

positioning a heat-shrink tube over an area of said stem section overlying said elongated tube;

shrinking said heat-shrink tube;

folding a length of said stem section over said heat-shrink tube;

overlaying a compression tube onto an overtube to create an overtube assembly;

mounting said overtube assembly onto a section of said elongated tube, the stem section length folded over said heat-shrink tube, and the stem section overlying said elongated tube;

heating and subsequently cooling said overtube assembly whereby said overtube forms a mechanical attachment to said stem section folded over said heat-shrink tube and overlying said elongated tube; and securing a proximal end of said overtube onto said elongated tube.

2. The method of assembling a cavity measurement device of claim 1 wherein said elongated tube is made of a thermoplastic.

3. The method of assembling a cavity measurement device of claim 2 wherein said elongated tube is made of polyethylene terephthalate.

4. The method of assembling a cavity measurement device of claim 1 wherein the shrinking step comprises applying heat to said heat-shrink tube.

5. The method of assembling a cavity measurement device of claim 4 wherein said heat-shrink tube is made of polyvinylidene fluoride.

6. The method of assembling a cavity measurement device of claim 1 wherein said overtube is made of polyethylene terephthalate.

7. The method of assembling a cavity measurement device of claim 1 wherein a distal end of said overtube assembly and said distal end of said elongated tube are aligned at said bulbous portion of said silicone balloon.

8. The method of assembling a cavity measurement device of claim 1 further comprising the step of removing said compression tube from said overtube.

9. The method of assembling a cavity measurement device of claim 1 wherein said mechanical attachment is leakproof.

10. The method of assembling a cavity measurement device of claim 9 wherein said mechanical attachment withstands a 45 psi balloon pressure.

11. The method of assembling a cavity measurement device of claim 9 wherein said mechanical attachment has an attachment strength greater than the balloon material tensile strength.

12. The method of assembling a cavity measurement device of claim 1 wherein the overlaying step comprises:
expanding the compression tube; and
inserting the overtube into the expanded compression tube to form said overtube assembly.

13. A method of assembling a cavity measurement device comprising the steps of:
providing an elastic balloon having a proximal tubular stem section extending from a stem section proximal end distally through a stem section length and a distal bulbous portion extending from a stem section distal end;
providing an elongated tube extending from a tube proximal end to a tube distal end;

inserting said elongated tube into said tubular stem section to dispose said stem section over at least a distal section of said elongated tube;

positioning a heat-shrink tube having a length shorter than the stem section length over an area of said stem section intermediate the stem section proximal and distal ends;

shrinking said heat-shrink tube against the area of said stem section;

folding a length of said stem section extending proximally from said heat-shrink tube distally over said heat-shrink tube to extend the folded length and stem section proximal end toward the distal bulbous portion;

compressing an overtube onto and overlying the stem section overlying said elongated tube, the folded length of the stem section and proximally from said heat shrink tube around a section of said elongated tube; and securing a proximal end of the overtube onto said elongated tube.

14. The method of assembling a cavity measurement device of claim 13 wherein the compressing step comprises:
providing said overtube and an elastic compression tube;
overlaying the compression tube onto the overtube to create an overtube assembly;
mounting the overtube assembly onto said stem section overlying said heat-shrink tube and said elongated tube to extend along the folded length of said stem section and proximally from said heat shrink tube around a section of said elongated tube;
heating said overtube assembly to soften and compress the overtube; and
cooling said overtube assembly, whereby the overtube forms a mechanical attachment to said stem section extending distally over said heat-shrink tube and said elongated tube.

15. The method of assembling a cavity measurement device of claim 14 further comprising the step of removing said compression tube from said overtube.

16. The method of assembling a cavity measurement device of claim 14 wherein the overlaying step comprises:
expanding the elongated elastic compression tube; and
inserting the overtube into the expanded compression tube to form said overtube assembly.

17. The method of assembling a cavity measurement device of claim 14 wherein the mounting step comprises aligning a distal end of said overtube assembly with said distal end of said elongated tube adjacent said bulbous portion of said elastic balloon.

18. The method of assembling a cavity measurement device of claim 13 wherein said bulbous portion of said elastic balloon is formed of silicone.

19. The method of assembling a cavity measurement device of claim 13 wherein said mechanical attachment is leak proof.

20. The method of assembling a cavity measurement device of claim 13 wherein said mechanical attachment withstands a 45 psi balloon pressure.

* * * * *